United States Patent [19]
Cooper

[11] Patent Number: 5,248,681
[45] Date of Patent: Sep. 28, 1993

[54] DIHYDROPYRIDINE ANTIALLERGY AGENTS

[75] Inventor: Kelvin Cooper, Noank, Conn.

[73] Assignee: Pfizer Inc., New York, N.Y.

[21] Appl. No.: 768,578

[22] PCT Filed: Mar. 14, 1990

[86] PCT No.: PCT/EP90/00432
§ 371 Date: Sep. 19, 1991
§ 102(e) Date: Sep. 19, 1991

[87] PCT Pub. No.: WO90/12015
PCT Pub. Date: Oct. 18, 1990

[30] Foreign Application Priority Data
Apr. 1, 1989 [GB] United Kingdom ............... 8907401

[51] Int. Cl.$^5$ ............... A61K 31/505; C07D 471/04
[52] U.S. Cl. ..................... 514/258; 514/290; 514/300; 514/302; 514/303; 544/279; 546/111; 546/113; 546/117; 546/119; 546/165
[58] Field of Search .................... 544/279; 514/258

[56] References Cited
FOREIGN PATENT DOCUMENTS
299727  1/1989  European Pat. Off. .

Primary Examiner—Thurman K. Page
Assistant Examiner—Jyothsna Venkat
Attorney, Agent, or Firm—Peter C. Richardson; Gregg C. Benson; Mervin E. Brokke

[57] ABSTRACT

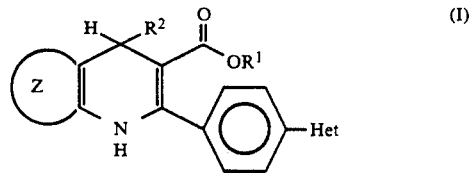

Platelet activating factor antagonists of formula (I), in which $R^2$ is optionally substituted phenyl, $R^1$ is H, alkyl or arylalkyl, Het is an optionally substituted N-containing heterocyclic group optionally fused to a phenyl or a further heterocyclic ring, and Z completes an optionally substituted carbocyclic or heterocyclic ring having a carbonyl group attached to the 5-position of the dihydropyridine ring. The compounds are useful for treating allergic and inflammatory conditions.

7 Claims, No Drawings

DIHYDROPYRIDINE ANTIALLERGY AGENTS

This invention relates to dihydropyridines, specifically to certain 1,4-dihydropyridines which are useful in the treatment of allergic and inflammatory conditions in humans and animals.

A number of 1,4-dihydropyridines have been previously described as antiischaemic and antihypertensive agents. These compounds are able to inhibit the movement of calcium into cells and are thus active in the treatment or prevention of a variety of cardiac conditions or as antihypertensive agents. (See for example EP-A-100189.) However the compounds of the present invention are potent and selective antagonists of platelet activating factor and as such they have clinical utility in a quite different area, namely for treating allergic and inflammatory conditions such as asthma and arthritis respectively.

Platelet activating factor (PAF) 1-O-alkyl-2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. In vitro, PAF stimulates the movement and aggregation of neutrophils and the release therefrom of tissue-damaging enzymes and oxygen radicals. These activities contribute to actions of PAF in vivo consistent with it playing a significant role in inflammatory and allergic responses. Thus, intradermal PAF has been shown to induce an inflammatory response, with associated pain, accumulation of inflammatory cells and increased vascular permeability, comparable with the allergic skin reaction following exposure to allergen. Similarly, both the acute broncho-constriction and chronic inflammatory reactions elicited by allergens in asthma can be mimicked by intratracheal administration of PAF. Accordingly agents which antagonise the actions of PAF and, consequently also prevent mediator release by PAF, will have clinical utility in the treatment of a variety of allergic, inflammatory and hypersecretory conditions such as asthma, arthritis, rhinitis, bronchitis and urticaria.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock. Intravenous infusion of PAF at doses of 20–200 pmol $kg^{-1}$ $min^{-1}$ into rats results in the formation of extensive haemorrhagic erosions in the gastric mucosa and thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role in the disease of psoriasis. And finally, increasing evidence supports a potential pathophysiological role for PAF in cardiovascular disease. Thus recent studies in angina patients show PAF is released during atrial pacing. Intracoronary injection of PAF in pigs induces a prolonged decrease in coronary flow and, in guinea pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke.

Thus the compounds of the invention, by virtue of their ability to antagonise the actions of PAF, are likely to be of value in the treatment of any of the above conditions.

Our copending published-patent applications EP-A-258033, EP-A-266989, EP-A-299727 and EP-A-310386 disclose 4-aryl-1,4-dihydropyridines as PAF antagonists.

According to the present invention there are provided compounds of the formula (1) and pharmaceutically acceptable salts thereof

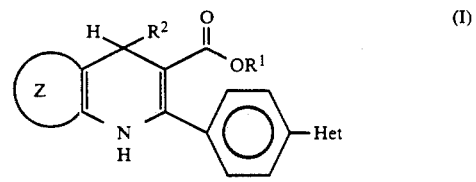

wherein
R² is phenyl or phenyl substituted by one or more substituents independently selected from nitro, halo, $C_1$-$C_4$ alkyl, $C_1$-$C_4$ alkoxy, aryl($C_1$-$C_4$)alkoxy, perfluoro($C_1$-$C_4$) alkoxy, $C_1$-$C_4$ alkylthio, $C_1$-$C_4$ alkylsulphonyl, hydroxy, trifluoromethyl and cyano, or is phenyl fused to a dioxolane ring;
R¹ is selected from H, $C_1$-$C_6$ alkyl and aryl($C_1$-$C_4$)alkyl;
Het is a 5- or 6-membered aromatic heterocyclic group containing one or more nitrogen atoms in its ring which ring may be optionally fused to a benzene ring or to a further 5- or 6-membered aromatic heterocyclic ring containing one or more nitrogen atoms, at least one of said heterocyclic rings optionally also containing an oxygen or sulphur atom and being optionally substituted with one or more substituents independently selected from $C_1$-$C_4$ alkyl, $C_1$-$C_4$ alkoxy, halo, trifluoromethyl and cyano; and
Z completes a 5- or 6-membered carbocyclic or heterocyclic ring having a carbonyl group attached to the 5-position of the dihydropyridine ring, said carbocyclic or heterocyclic ring optionally being substituted, in addition to said carbonyl group, by up to three substituents independently selected from $C_1$-$C_4$ alkyl, $C_3$-$C_7$ cycloalkyl, aryl ($C_1$-$C_4$) alkyl, amino and oxo or being fused to a benzene ring; the ring completed by Z, when heterocyclic, containing one oxygen or one or two nitrogen atoms.

In the above definitions "halo" means fluoro, chloro, bromo or iodo and "aryl" means phenyl optionally substituted by one or more substituents each independently selected from halo, trifluoromethyl, $C_1$-$C_4$ alkyl, hydroxy, $C_1$-$C_4$ alkoxy, ($C_1$-$C_4$ alkoxy) carbonyl, sulphamoyl and cyano. Alkyl and alkoxy groups containing 3 or more carbon atoms may be straight or branched chain.

$R^2$ is preferably 2-chlorophenyl, 2-trifluoromethoxyphenyl, 2,4-difluorophenyl, 4-cyanophenyl or 1,3-benzodioxol-4-yl.

Preferably Z is selected from the following:

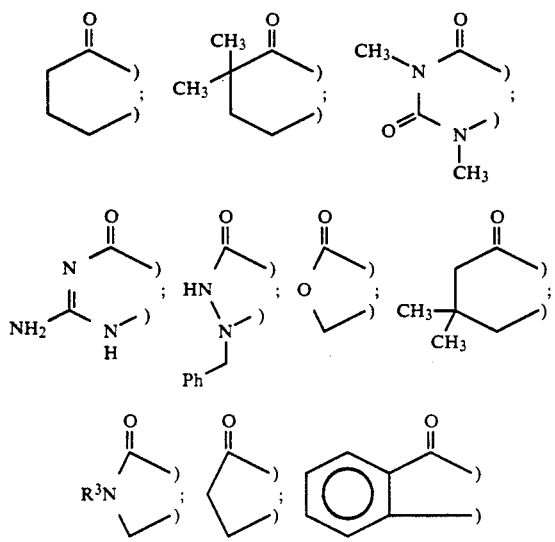

wherein $R^3$ is H, $C_1$-$C_4$ alkyl, $C_3$-$C_7$ cycloalkyl or aryl ($C_1$-$C_4$)alkyl. Most preferably, $R^3$ is H, cyclohexyl or benzyl.

Het may be a 1,2,4-triazolyl group optionally substituted with one or two $C_1$-$C_4$ alkyl groups, or an imidazolyl group optionally substituted with up to three halogens or $C_1$-$C_4$ alkyl groups or optionally substituted with a $C_1$-$C_4$ alkyl or $CF_3$ group and fused to a benzene or pyridine or pyrimidine ring which may be substituted with one or more $C_1$-$C_4$ alkyl or $C_1$-$C_4$ alkoxy or halogen groups. Het may alternatively be a pyridyl group optionally substituted with from one to three $C_1$-$C_4$ alkyl or $CF_3$ groups.

Alternatively, Het may be an oxazolyl or thiazolyl group optionally substituted with up to two $C_1$-$C_4$ alkyl groups, or an imidazolyl group optionally substituted with a $C_1$-$C_4$ alkyl or $CF_3$ group and fused to an oxazolyl or thiazolyl ring.

Het is more preferably 2-methylimidazo[4,5-c]pyrid-1-yl, imidazo]-1-yl, benzimidazol-1-yl, 2-methylbenzimidazol-1-yl, 3,5-dimethyl-1,2,4-triazol-4-yl, 2-trifluoromethylimidazo[4,5-c]pyrid-1-yl, 2-butylimidazo[4,5-c]pyrid-1-yl, 2-methylimidazo[4,5-b]pyrid-3-yl, 2-methylimidazo[1,2-a]pyrid-3-yl, 2-ethylimidazo[4,5-c]pyrid-1-yl, 7-methoxy-2-methylimidazo[4,5-d]pyrimid-3-yl, 2-methylimidazo[4,5-c]pyrid-3-yl, 2,4,6-trimethylimidazo[4,5-c]pyrid-1-yl, 2,4-dimethylimidazol-1-yl, 2-methylimidazol-1-yl, 2,4,5-trimethylimidazol-1-yl, 4-methylimidazol-1-yl, 2-methylpyrid-3-yl, 2,6-dimethylpyrid-3-yl, 3,5-dimethyl-1,2,4-triazol-1-yl, 4-methyloxazol-5-yl, 2,4-dimethylthiazol-5-yl, 6-methylimidazo[1,2-b]thiazol-5-yl, or 4-methylthiazol-5-yl.

A particularly preferred compound is 8-(2-chlorophenyl)-2,4-dimethyl-7-ethoxycarbonyl-1,2,3,4,5,8-hexahydro-6-[4-(2-methylimidazo[4,5-c]pyrid-1-yl)phenyl]-pyrido-[2,3-d]pyrimidin-1,3-dione.

The compounds of formula (I) contain at least one asymmetric centre and will therefore exist as one or more pairs of enantiomers, and such pairs of individual isomers may be separable by physical methods, e.g. by fractional crystallisation or chromatography of the parent compounds or of a suitable salt or derivative thereof. Alternatively, particular isomers may be prepared using the corresponding optical isomers of the precursors used in preparation of compounds of the invention. The invention includes all the enantiomers of the compounds of formula (I) whether separated or not.

The pharmaceutically acceptable acid addition salts of the compounds of formula (1) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate, tartrate, methanesulphonate and benzenesulphonate.

The compounds of formula (I) may be obtained by a number of different processes in accordance with the invention:

(a) In one process, the compounds are obtained by Hantzsch synthesis, according to the following reaction scheme:

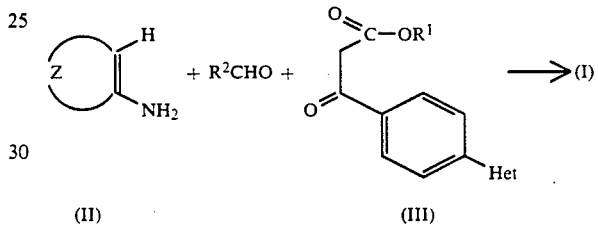

(II)          (III)

wherein $R^1$, $R^2$, Z and Het are as previously defined.

In a typical procedure, the ketoester (III) and aldehyde are heated under reflux, in a suitable organic solvent, e.g. a $C_1$-$C_4$ alkanol such as ethanol, with the compound of formula (II) for up to 16 hours. The product of the formula (I) can then be isolated and purified by conventional procedures, for example by partition, recrystallisation or chromatography.

Alternatively, the keto-ester of formula (III) and the aldehyde are allowed to react together, typically by stirring a slight excess of ketoester with the aldehyde at room temperature for 48 hours in a suitable organic solvent, such as isopropyl alcohol containing pyridine as a catalyst, to give an intermediate compound of formula (IV):

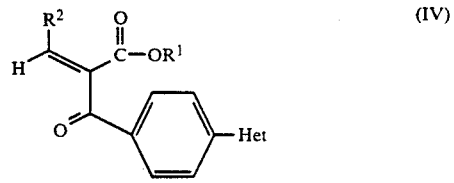

(IV)

If desired, the intermediate compound may be isolated, for example by evaporating the reaction mixture, triturating the residue and purifying the product by filtration and recrystallisation for a suitable solvent. The compound of formula (IV) may then be reacted with compound (II), for example by heating the compounds together in an alcoholic solvent at 60°-130° C. and preferably under reflux, to produce the compound of formula (I). The compound so produced may be isolated by conventional methods.

The keto-esters of formula (III) are either known compounds or may be prepared as described in U.S. Pat. No. 4,935,430, which is incorporated herein by reference.

The compounds of formula (II) are either known compounds or can be prepared by conventional procedures.

The aldehydes $R^2CHO$ are either known or can be prepared by known methods in accordance with literature precedents.

(b) In an alternative procedure, the compounds of formula (I) in which Z is

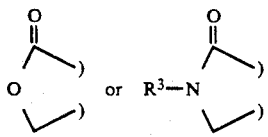

where $R^3$ is H, $C_1$-$C_4$ alkyl, $C_3$-$C_7$ cycloalkyl or aryl($C_1$-$C_4$)alkyl, are prepared from a compound of formula (V):

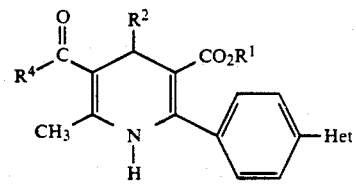

wherein $R^4$ is $C_1$-$C_6$ alkyl (such as methyl) or aryl(-$C_1$-$C_4$)alkyl by stirring at 0° C. under nitrogen with pyridinium bromide perbromide and pyridine in chloroform for about 1 hour, optionally followed by addition of the appropriate amine $R^3NH_2$, e.g. cyclohexylamine, benzylamine or ammonia. The mixture is then refluxed for up to 3 hours. The product of formula (T) can then be isolated and purified by conventional procedures, for example partition, recrystallisation or by chromatography.

The starting materials of formula (V) are prepared by conventional methods, for example by the Hantzsch synthesis described under (a).

(c) In a further alternative procedure, the compounds of formula (I) in which Z is:

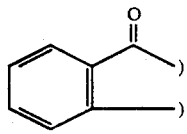

may be prepared by reaction of a compound of formula (VI):

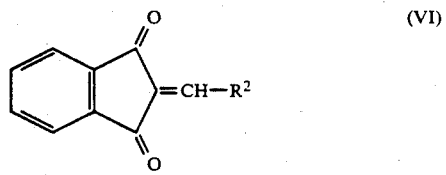

with the compound of formula (III) from (a) in the presence of an ammonium salt, for example by refluxing in the presence of ammonium acetate and glacial acetic acid for about 5 minutes. The product is then neutralised and isolated and purified by conventional procedures, e.g. by chromatography.

The activity of the compounds of the invention is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6 mM $Na_2HPO_4$, 100 mM NaCl, 0.1% glucose and 0.1% bovine serum albumin, pH 7.25) and finally resuspended in buffer solution to a concentration of $2 \times 10^8$ platelets/ml. A sample (0.5 ml) is preincubated for two minutes at 37° C. in a Paton aggregometer with stirring, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 μg/kg) and DL-propranolol (5 mg/kg) in 0.9% w/v sodium chloride is injected (0.2 ml) via a tail vein into mice. The compounds under test are either injected into the tail vein immediately prior to the PAF/propranolol injection or administered orally by gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs. In this test airways resistance and dynamic lung compliance are calculated from recordings of airflow and transpleural pressure and calculation of tidal volume. The bronchoconstriction induced by PAF (100 ng/kg) is determined. One hour after the initial dose of PAF the compound under test is administered and the test repeated. The ability of the compound to reduce the bronchoconstrictor effect of PAF is recorded as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2–1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus in a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I), or a pharmaceutically acceptable salt thereof, for use in medicine, in particular in the treatment of allergic and inflammatory conditions in a human being.

The preparation of the compounds of the invention is further illustrated by the following Example.

EXAMPLE 8-(2-Chlorophenyl)-2,4-dimethyl-6-ethoxycarbonyl-1,2,3,4,5,8-hexahydro-6-[4-(2-methylimidazo[4,5-c]pyrid-1-yl)phenyl]-pyrido[2,3-d]pyrimidin-1,3-dione

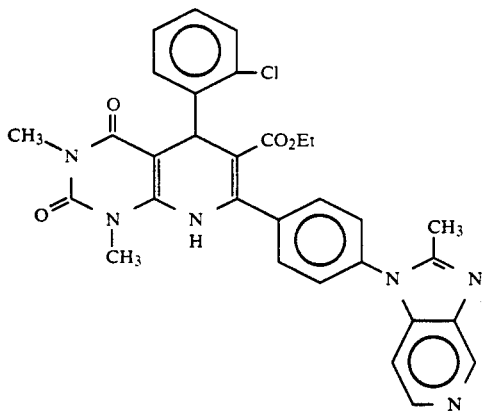

A mixture of 6-amino-1,3-dimethyluracil (310 mg, 2.0 mmol), 2-chlorobenzaldehyde (280 mg, 2.0 mmol) and ethyl 4'-(2-methylimidazo[4,5-c]pyrid-1-yl)benzoylacetate (647 mg, 2.0 mmol) in ethanol (8 ml) was heated under nitrogen at reflux for 14 hours. The mixture was cooled and filtered. The solid was stirred in dichloromethane and the insoluble material was filtered off. The filtrate was concentrated under reduced pressure and the residue was triturated with ethanol to give the title compound (46 mg, 4%) as a tan solid, m.p. 216°–219° C.

Analysis % Found: C,61.13; H,4.86; N,13.82. $C_{31}H_{27}ClN_6O_4.3/2H_2O$ requires: C,61.03; H,4.95; N,13.77.

PREPARATION 1

Ethyl 4'-(2-methylimidazo[4,5-c]pyrid-1-yl)benzoyl acetate

Method A

Essentially the method of Y. Kishi, S. M. Hannick, *J. Org. Chem.*, 1983, 48, 3833.

Zinc dust (894 mg, 13.7 mmol) was suspended in dry tetrahydrofuran (3 ml) under nitrogen and sonicated at room temperature for 10 minutes. Ethyl bromoacetate (2 drops) was added and the mixture was refluxed for 5 minutes. A solution of 1-(4-cyanophenyl)-2-methylimidazo[4,5-c]pyridine (640 mg, 2.74 mmol) in dry tetrahydrofuran (6 ml) was added and the mixture was refluxed for 5 minutes. A solution of ethyl bromoacetate (1.822 g, 10.94 mmol) in dry tetrahydrofuran (2 ml) was added dropwise over 1 hour at reflux, and after a further 10 minutes, the mixture was allowed to cool to room temperature. 50% aqueous potassium carbonate (1 ml) was added and the mixture was stirred for 45 minutes at room temperature, and then filtered through Arbocel filter aid, washing with THF. The filtrate was concentrated under reduced pressure to give a yellow gum. This material was treated with a mixture of 20% aqueous trifluoro acetic acid (10 ml) and dichloromethane (50 ml) at room temperature for 15 minutes. The mixture was neutralised by the addition of saturated aqueous sodium, hydrogen carbonate, and then extracted with dichloromethane (2×30 ml). The combined extracts were dried ($MgSO_4$), concentrated under reduced pressure, and the crude product was purified by flash chromatography (eluting with 10–20% methanol in ethyl acetate) to give ethyl 4'-(2-methylimidazo[4,5-c]pyrid-1-yl)benzoylacetate (480 mg, 54%) as a yellow gum.

Material obtained by Method A was a white solid, m.p. 111°–112° C., (after recrystallisation from ethyl acetate).

$^1$H-NMR (300 MHz, $CDCl_3$) 1.32 (3H, t, J 6 Hz), 2.61 (3H, s), 4.09 (2H, s), 4.28 (2H, q, J 6 Hz), 7.16 (1H, d, J 6 Hz), 7.55 (2H, d, J 9 Hz), 8.23 (2H, d, J 9 Hz), 8.46 (1H, d, J 6 Hz), 9.09 (1H, s).

Method B (a) 4-(4-Acetylphenyl)amino-3-nitropyridine hydrochloride

A solution of 4-chloro-3-nitropyridine hydrochloride (9.75 g, 50 mmol) in ethanol (40 ml) was added to a slurry of p-aminoacetophenone (6.76 g, 50 ml) in ethanol (25 ml), and the mixture was stirred at room temperature overnight. The mixture was chilled in ice, and the yellow solid filtered off and dried in vacuo. Yield 10.1 g (69%), m.p. 197°–200° C.

$^1$H-NMR (300 MHz, DMSO-$d_6$) 2.61 (3H, s), 7.19 (1H, d, J 7 Hz), 7.53 (2H, d, J 8 Hz), 8.07 (2H, d, J 8 Hz), 8.33 (1H, d, J 7 Hz), 9.36 (1H, s), 10.74 (1H, s).

(b) 4-(4-Acetylphenyl)amino-3-aminopyridine 4-(4-Acetylphenyl)amino-3-nitropyridine hydrochloride (2.0 g, 71.8 mmol) was partitioned between aqueous sodium hydroxide and dichloromethane (3×20 ml). The combined organic phases were washed with water (20 ml) and concentrated under reduced pressure to give a solid. Ethanol (20 ml) was added, and the solution was hydrogenated over 5% palladium on carbon (0.2 g) at 50 p.s.i. (345 kPa) for 3.5 hours. The catalyst was filtered off, and the solvent removed under reduced pressure to give a brown solid, (1.8 g) which was used directly for the next reaction without purification, m.p. 165°–166° C. (after recrystallisation from ethanol).

$^1$H-NMR (300 MHz, DMSO-d$_6$) 2.47 (3H, s), 5.00 (2H, br.s), 7.04 (3H, m), 7.70 (1H, br.s), 7.83 (2H, d, J 8 Hz), 7.98 (1H, br.s), 8.12 (1H, s).

(c) 1-(4-Acetyl)phenyl-2-methylimidazo[4,5-c]pyridine

A solution of 4-(4-acetylphenyl)amino-3-aminopyridine (68.0 g, 0.3 mmol) in acetic acid (204 ml) and acetic anhydride (204 ml) was heated at 95° C. for 1.5 hours then cooled and concentrated under reduced pressure. The residue was dissolved in water (500 ml) and rendered basic by the addition of saturated aqueous ammonia. The product was filtered off, washed with water (2×100 ml) and dried in vacuo to give the title compound, (61.0 g, 81%) as a brown solid, m.p. 155°–156° C. (after recrystallisation from water).

$^1$H-NMR (300 MHz, CDCl$_3$), 2.59 (3H, s), 2.72 (3H, s), 7.12 (1H, d, J 5 Hz), 7.53 (2H, d, J 8 Hz), 8.22 (2H, d, J 8 Hz), 8.40 (1H, d, J 5 Hz), 9.04 (1H, s).

(d) Ethyl 4'-(2-methylimidazo[4,5-c]pyrid-1-yl]benzoylacetate

A solution of 1-(4-acetyl)phenyl-2-methylimidazo[4,5-c]-pyridine (17.5 g, 69.7 mmol.) in dry tetrahydrofuran (175 ml) was added to a slurry of sodium hydride (3.68 g, 153 mmol) in a mixture of dry tetrahydrofuran (35 ml) and diethyl carbonate (24.7 g, 209 mmol) at reflux with stirring over 45 minutes. After a further 1 hour, the mixture was cooled, hexane (200 ml) was added and the resulting precipitate was filtered off and washed with hexane (2×100 ml). The solid was suspended in ethyl acetate (200 ml) and acetic acid (10.2 g) was added. After being stirred for 15 minutes, water (200 ml) was added, and the organic layer was separated. The aqueous phase was extracted with ethyl acetate (100 ml) and the combined organic solutions were washed with water (200 ml), dried (MgSO$_4$) and concentrated to give a gum (17.3 g, 77%). This material could be further purified if desired by flash chromatography (eluting with ethyl acetate:methanol=7:1) to give the title compound as a white solid.

Method C (a) 4-(2-Methylimidazo[4,5-c]pyrid-1-yl)benzoic acid

A mixture of 1-(4-cyanophenyl)-2-methylimidazo[4,5-c]pyridine (12.0 g, 51.3 mmol) and 40% aqueous sodium hydroxide (55 ml) in absolute ethanol (55 ml) was heated at reflux for 1½ hours. The solvent was removed under reduced pressure, and the brown residue was dissolved in water. The solution was chilled to 0° C. by the addition of ice. Glacial acetic acid (ca 33 ml) was added slowly. The buff solid which precipitated was filtered off, washed with water, and dried in vacuo at 70° C. Yield 9.14 g (70%).

$^1$H-NMR (300 MHz, DMSO-d$_6$) 2.49 (3H, s), 7.25 (1H, d, J 6 Hz), 7.72 (2H, d, J 6 Hz), 8.17 (2H, d, J 6 Hz), 8.30 (1H, d, J 6 Hz), 8.92 (1H, s).

(b) Ethyl 4'-(2-methylimidazo[4,5-c])pyrid-1-yl)benzoyl acetate

Oxalyl chloride (37.0 ml, 184 mmol) was added to a mixture of 4-(2-methylimidazo[4,5-c]pyrid-1-yl) benzoic acid (11.64 g, 46 mmol) and dry dimethylformamide (0.2 ml) in dry dichloromethane (200 ml) under nitrogen with ice cooling. At the end of the addition, the mixture was sonicated for 1 hour at room temperature, and then concentrated under reduced pressure and re-suspended in dry dichloroethane (200 ml).

In a separate flask, isopropylmagnesium chloride (137 ml of a 2M solution in tetrahydrofuran, 274 mmol) was added dropwise over 20 minutes to a solution of ethyl malovic acid (18.14 g, 137 mmol) in dry dichloromethane (100 ml) at 0° C. After a further 20 minutes, the solution was added at room temperature to the suspension of the acid chloride generated above. The red mixture was sonicated at room temperature for 30 minutes and then cooled in ice whilst 4N hydrochloric acid (250 ml) was added. The mixture was stirred for 20 minutes at room temperature, diluted with dichloromethane (200 ml), and the layers were separated. The aqueous layer was neutralised with saturated aqueous sodium bicarbonate, and extracted with dichloromethane (3×200 ml). The combined extracts were dried (MgSO$_4$) and concentrated under reduced pressure to give a yellow gum., which crystallised slowly on standing. Yield 12.10 g (80%).

PREPARATION 2

1-(4-Cyanophenyl)-2-methylimidazo[4,5-c]pyridine (a) N-(4-Cyanophenyl)-4-amino-3-nitropyridine According to the method of *J. C. S. Perkin Trans. I,* 1979, 135, p-cyanoaniline (6.894 g, 58.4 mmol) was added to a solution of 4-chloro-3-nitropyridine (9.26 g, 58.4 mmol) in ethanol (200 ml) and the mixture was stirred at room temperature for 18 hours. The resulting yellow suspension was poured into 500 ml of ice-cold dilute ammonia and filtered. The solid was treated with 150 ml of boiling ethanol, cooled in ice, and filtered to give N-(4-cyanophenyl)-4-amino-3-nitropyridine, 12.15 g, as a bright yellow powder, m.p. 210°–211° C.

$^1$H-NMR (300 MHz, CDCl$_3$) 7.15 (1H, d, J 6 Hz), 7.45 (2H, d, J 9 Hz), 7.79 (2H, d, J 9 Hz), 8.43 (1H, d, J 6 Hz), 9.36 (1H, s), 9.80 (1H, br, s).

(b) 3-Amino-4-(4'-cyanophenyl)aminopyridine

According to a modification of the method of *Pharm. Helv. Acta,* 1975, 50, 188., tin dichloride dihydrate (56.4 g, 250 mmol) was added to a suspension of N-(4-cyanophenyl)-4-amino-3-nitropyridine (12.0 g, 50 mmol) in 2N aqueous hydrochloric acid (35 ml), water (150 ml) and ethanol (75 ml) and the resulting mixture was heated to reflux for 10 minutes under nitrogen. The mixture was cooled in ice, poured into ice-cold 2N aqueous sodium hydroxide (400 ml) and filtered. The creamy-coloured solid was washed with 2N aqueous sodium hydroxide and water, and then dried in a vacuum desiccator. The product, 3-amino-4-(4'-cyanophenyl)-aminopyridine, 9.31 g, gradually turns reddish brown on exposure to light and air.

$^1$H-NMR (300 MHz, CDCl$_3$) 3.52 (2H, br s), 6.04 (1H, br s), 7.03 (2H, d, J 9 Hz), 7.59 (2H, d, J 9 Hz), 8.07 (1H, m), 8.20 (1H, s).

(c) 1-(4-Cyanophenyl)-2-methylimidazo[4,5-c]pyridine

A mixture of 3-amino-4-(4'-cyanophenyl)aminopyridine (9.31 g, 44.3 mmol), triethyl-orthoacetate (40 ml) and acetic anhydride (30 ml) was heated at reflux for 2 hours under nitrogen, cooled, then concentrated under reduced pressure. The brown residue was dissolved in 1M hydrochloric acid and washed with ethyl acetate (200 ml). The aqueous layer was rendered basic with saturated aqueous ammonia and extracted with dichloromethane (3×200 ml). The combined extracts were washed with water, dried (MgSO4) and concentrated to give 1-(4-cyanophenyl)-2-methylimidazo[4,5-c]pyridine, 6.5 g, as a brown solid.

¹H-NMR (300 MHz, CDCl₃) 2.61 (3H, s), 7.13 (1H, d, J 6 Hz), 7.58 (2H, d, J 9 Hz), 7.98 (2H, d, J 9 Hz), 8.45 (1H, d, J 6 Hz), 9.11 (1H, s).

I claim:

1. A compound of formula (I) or a pharmaceutically acceptable salt thereof:

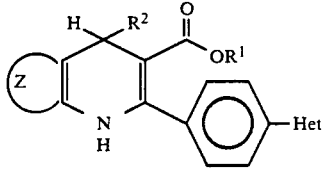

(I)

wherein
R² is selected from the group consisting of phenyl, phenyl substituted by one or more substituents independently selected from the group consisting of nitro, halo, C₁–C₄ alkyl, C₁–C₄ alkoxy, aryl(-C₁–C₄)alkoxy, perfluoro(C₁–C₄)alkoxy, C₁–C₄ alkylthio, C₁–C₄ alkylsulphonyl, hydroxy, trifluoromethyl and cyano, and phenyl fused to a dioxolane ring;

R¹ is selected from the group consisting of H, C₁–C₆ alkyl and aryl(C₁–C₄)alkyl;

Het is either
(a) a 1,2,4-triazolyl group optionally substituted with one or two C₁–C₄ alkyl groups, or an imidazolyl group optionally substituted by one, two or three halogens or C₁–C₄ alkyl groups or optionally substituted with a C₁–C₄ alkyl or CF₃ group or fused to a benzene or pyridine or pyrimidine ring which may be substituted with one or more C₁–C₄ alkyl or C₁–C₄ alkoxy or halogen groups, or
(b) a pyridyl group optionally substituted by one, two or three C₁–C₄ alkyl or CF₃ groups, or
(c) an oxazolyl or thiazolyl group optionally substituted by one or two C₁–C₄ alkyl groups, or an imidazolyl group optionally substituted with a C₁–C₄ alkyl or CF₃ group or fused to an oxazolyl or thiazolyl ring; and Z is selected from the group consisting of optionally substituted pyrimidine-4-one and pyrimidine-2,4-dione; where Z is optionally substituted by one, two or three substituents, where each substituent is independently selected from the group consisting of C₁–C₄ alkyl, C₃–C₇ cycloalkyl, aryl(C₁–C₄)alkyl, oxo and amino.

2. A compound according to claim 1 wherein Z is

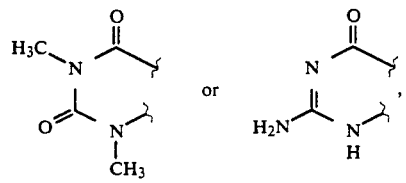

3. A compound according to claim 1, in which R² is 2-chlorophenyl, 2-trifluoromethoxyphenyl, 2,4-difluorophenyl, 4-cyanophenyl or 1,3-benzodioxol-4-yl.

4. A compound according to claim 1, in which "Het" is 2-methylimidazo[4,5-c]pyrid-1-yl, imidazol-1-yl, benzimidazol-1-yl, 2-methylbenzimidazol-1-yl, 3,5-dimethyl-1,2,4-triazol-4-yl, 2-trifluoromethylimidazo-[4,5-c]pyrid-1-yl, 2-butylimidazo[4,5-c]pyrid-1-yl, 2-methylimidazo[4,5-b]pyrid-3-yl, 2-methylimidazo[1,2-a]pyrid-3-yl, 2-ethylimidazo[4,5-c]pyrid-1-yl, 7-methoxy-2-methylimidazo[4,5-d]pyrimid-3-yl, 2-methylimidazo[4,5-c]pyrid-3-yl, 2,4,6-trimethylimidazo[4,5-c]pyrid-1-yl, 2,4-dimethylimidazol-1-yl, 2-methylimidazol-1-yl, 2,4,5-trimethylimidazol-1-yl, 4-methylimidazol-1-yl, 2-methylpyrid-3-yl, 2,6-dimethylpyrid-3-yl, 3,5-dimethyl-1,2,4-triazol-1-yl, 4-methyloxazol-5-yl, 2,4-dimethylthiazol-5-yl, 6-methylimidazo[1,2-b]thiazol-5-yl, or 4-methylthiazol-5-yl.

5. 8-(2-chlorophenyl)-2,4-dimethyl-7-ethoxycarbonyl-1,2,3,4,5,8-hexahydro-6-[4-(2-methylimidazo[4,5-c]pyrid-1-yl)phenyl]-pyrido-[2,3-d]pyrimidin-1,3-dione.

6. A pharmaceutical composition comprising a compound according to claim 1 and a pharmaceutically acceptable carrier or diluent.

7. A method of treating allergic or inflammatory conditions, which comprises administering to a patient an effective amount of compound according to claim 1.

* * * * *